(12) United States Patent
Ward

(10) Patent No.: US 6,369,115 B1
(45) Date of Patent: Apr. 9, 2002

(54) STABILIZED POWDER FORMULATIONS

(75) Inventor: Gary Ward, San Diego, CA (US)

(73) Assignee: Dura Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/528,519

(22) Filed: Mar. 20, 2000

(51) Int. Cl.$^7$ .................. A61K 31/045; A61K 9/14; A61K 31/075; A61K 31/56; A61K 31/135; A61K 47/26

(52) U.S. Cl. .................. 514/728; 424/489; 424/499; 514/169; 514/171; 514/177; 514/178; 514/179; 514/180; 514/181; 514/182; 514/646; 514/716; 514/717; 514/718; 514/721; 514/727; 514/728; 514/730; 514/731; 514/734; 514/736; 514/738; 514/777; 514/826; 514/951; 514/970

(58) Field of Search .................. 424/489, 499; 514/579, 646, 656, 657, 675, 690, 691, 706, 712, 715, 716, 717, 724, 727, 738, 777, 169, 171, 177, 178, 179, 180, 181, 182, 718, 721, 728, 730, 731, 734, 736, 826, 951, 970

(56) References Cited

U.S. PATENT DOCUMENTS

| | | | |
|---|---|---|---|
| 5,270,305 A | 12/1993 | Palmer | 514/171 |
| 5,674,860 A | 10/1997 | Carling et al. | 514/171 |
| 5,795,564 A | 8/1998 | Aberg et al. | 424/45 |
| 5,934,273 A | 8/1999 | Andersson et al. | 128/203 |
| 5,955,439 A * | 9/1999 | Green | 514/23 |
| 6,030,604 A * | 2/2000 | Trofast | 424/46 |

FOREIGN PATENT DOCUMENTS

GB    2 255 503 B    12/1995

* cited by examiner

*Primary Examiner*—Jose' G. Dees
*Assistant Examiner*—Frank Choi
(74) *Attorney, Agent, or Firm*—Lyon & Lyon LLP

(57) ABSTRACT

A dry powder formulation for treatment of pulmonary conditions, via inhalation, includes an effective amount of formoterol or a salt or solvate thereof, in a dry powder form, an effective amount of fluticasone, in a dry powder form, and an excipient. A method for preparing a physically stable dry powder formulation for inhalation includes the steps of micronizing a first active polar drug, a second active non-polar drug, and a polar excipient. The second non-polar active drug is first blended with the excipient to form an intermediate mixture. The intermediate mixture is then blended with the first active polar drug. The increased separation of the polar drug and polar excipient stabilizes the formulation.

12 Claims, No Drawings

STABILIZED POWDER FORMULATIONS

FIELD OF THE INVENTION

This invention relates to stabilized dry powder formulations used for treatment of respiratory conditions, such as asthma. The invention further relates to the use of a polar bronchodilator in combination with a less polar anti-inflammatory drug for treating respiratory conditions.

BACKGROUND OF THE INVENTION

Within the past 30 years, asthma has become increasingly prevalent, especially among children. Despite asthma drug therapy, asthma is still a serious and potentially fatal disease. Asthma is now recognized as a chronic inflammatory disease. A common cause for asthma attacks is poor compliance with long-term treatments, such as inhaled steroids. These do not provide immediate relief. On the other hand, patients will readily take bronchodilators using inhalers, since these provide rapid relief of symptoms.

Fluticasone propionate [(6 alpha, 11 beta, 16 alpha, 17 alpha)-6,9,-difluoro-11-hydroxy-16-methyl-3-oxo-17-(1-oxopropoxy)androsta-1,4-diene-17-carbothioic acid, S-fluoromethyl ester] is an anti-inflanmmatory drug. It has been used to reduce inflammation in airways. As a nasal spray it is used for rhinitis or inflammation of the nose. It has been used in inhalers for breathing problems like asthma, chronic bronchitis or emphysema.

Fluticasone propionate (referred to herein simply as "fluticasone") is a steroid which reduces the inflammation of nasal passages or bronchial tissue to make breathing easier. Its mechanism of the anti-inflammatory activity in general, is unclear. However, it is thought to act by the induction of phospholipase $A_2$ inhibitory proteins, collectively called lipocortins. It has been postulated that these proteins control the biosynthesis of potent mediators of inflammation such as prostaglandins and leukotrienes by inhibiting the release of their common precursor, arachidonic acid. Arachidonic acid is released from membrane phospholipids by phospholipase $A_2$. Chemically, fluticasone propionate is $C_{25}H_{31}F_3O_5S$. It is non-polar and insoluble in water.

Formoterol fumarate, (N-[2-hydroxy-5-[1-hydroxy-2-[[2-(4-methoxyphenyl)-1-methylethyl]amino]ethyl]phenyl] formamide), (referred to herein as "formoterol") is a long acting beta agonist which selectively stimulates $\beta_2$-receptors. It is a bronchodilator which relaxes the bronchial smooth muscle, making breathing easier. Inhaled formoterol acts rapidly, usually within minutes. Inhaled formoterol also exerts a prolonged bronchodilation, which in clinical trials has been demonstrated for up to 12 hours. Formoterol is polar and is soluble in water.

Most bronchodilators have relatively short duration of action. By using a compound with long duration e.g. formoterol, with an anti-inflammatory, such as fluticasone, improved therapy can be realized.

With these and other powder formulation drugs, physical stability is often difficult to maintain, when the powder is exposed to humidity in the environment, typically after the powder or dose container is removed from its sealed pouch or package. In the presence of water vapor, active powder drug particles used for inhalation, which are preferably in the 1–10 micron range, tend to fuse together into larger particles. As this occurs, the respirable dose is reduced, because the larger particles deposit out on the mouth, throat, or bronchi, and do not reach the deeper lung. This fusing of particles may occur more rapidly, and with greater detrimental effect, when the formulation has active and excipient particles, ( or two or more types of active drug particles) which are both polar, or which are both non-polar.

STATEMENT OF THE INVENTION

A dry powder formulation of formoterol, or a physiologically acceptable salt or solvate of formoterol, and fluticasone is delivered to the lung by inhalation. The formulation has higher efficiency and duration of bronchodilator action, as well as a rapid onset of action. This improves compliance for patients. Compliance is simplified as both drugs are delivered in a single dose, with a single dry powder inhaler. The rapid onset of the formoterol gives the patient immediate confirmation that a dose has been delivered. Overdosing is therefore reduced.

A dry powder inhaler provides a combined dose of formoterol and fluticasone for inhalation, to treat asthma or other respiratory conditions. Formoterol is polar and is soluble in water. Fluticasone is less polar or non-polar and is insoluble in water. Lactose, as a preferred excipient, is also polar. A more stable formulation is achieved by micronizing both the formoterol and the fluticasone. The lactose and fluticasone are then blended. This saturates the surface of the relatively larger polar lactose particles with the smaller and non-polar fluticasone particles. The active high energy sites on the lactose particles are largely occupied then by non-polar fluticasone particles. This blended mixture is then blended with the micronized formoterol particles. The physical stability of the resulting formulation is improved because the active particles are more physically separated from each other. Their propensity to fuse together is reduced, so that clumping, caking, or other formation of undesirable large agglomerations is reduced. The polar formoterol particles, which ordinarily would tend to fuse with the polar lactose particles, in the presence of water vapor in the environment, are inhibited from doing so, as they are separated from the high energy sites on the lactose particles by the previously blended in fluticasone. With formulations where there are more than one active drug, the most polar is first blended with the least polar, and then that blended combination is further blended with the remaining active drugs of moderate polarity.

This principle of preparing a stabilized formulation applies equally as well to other drug formulations having at least one more polar and at least one less polar active component.

A method of treating respiratory conditions includes the steps of, delivering, by inhalation of effective amounts of formoterol, or a salt or solvent of formoterol, and fluticasone.

Suitable physiologically salts of formoterol include acid addition salts derived from inorganic and organic acids, such as the hydrochloride, hydrobromide, sulphate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, salicylate, acetate succinate, lactate, glutarate, gluconate, tricarballylate, hydroxynaphthalenecarboxylate or oleate. These are referred to herein simply as "formoterol". Formoterol is preferably used in the form of its fumarate salt and as a dihydrate.

The ratio of formoterol to fluticasone is preferably within the range of 1:4 to 1:70.

The intended dose regimen is a twice daily administration, where the suitable daily dose of formoterol is in the range of 5 to 100 mcg with a preferred dose of 5–50 mcg and the suitable daily dose for fluticasone 10–100 mcg, and preferably 30–70 mcg.

A diluent or carrier, generally non-toxic and chemically inert to the medicament e.g. lactose, dextran, mannitol or glucose or any additives that will give the medicament a desired taste, can be added to the powder formulation In preparing the formulation, formoterol fumarate dihydrate and fluticasone are micronzied and mixed in the proportions given above. The optionally with the fluticasone blended with an excipient mixture is filled into a powder storage device, such as blister disks or cassettes, as described in U.S. Pat. Nos. 5,577,497 and 5,622,166, incorporated herein by reference.

What is claimed is:

1. A method for preparing a dry powder formulation for inhalation, comprising the sequential steps of:

micronizing a first active polar drug, and a second active non-polar drug;

blending the second non-polar active drug with a polar excipient to form an intermediate mixture, with the polar excipient comprising particles which are larger than the particles of the first and second active drugs created by the micronizing step; and blending the intermediate mixture with the first active polar drug.

2. The method of claim 1 where the first active polar drug comprises formoterol or a salt or solvate thereof, in a dry powder form.

3. The method of claim 2 where the formoterol comprises fomoterol fumarate dihydrate.

4. The method of claim 1 where the second active non-polar drug comprises fluticasone in a dry powder form.

5. The method of claim 1 where the first active polar drug comprises formoterol or a salt or solvate thereof, in a dry powder form, and the second active non-polar drug comprises fluticasone, in a dry powder form.

6. The method of claim 5 where the molar ratio of the formoterol to fluticasone ranges from 1:2 to 1:100.

7. The method of claim 6 where the molar ratio ranges from 1:4 to 1:60.

8. The method of claim 1 where the excipient comprises a member selected from the group consisting of lactose, dextran, mannitol, glucose, and a combination thereof.

9. The method of claim 1 where the micronized first and second particles have a size of 1–10 microns.

10. A method for preparing a dry powder formulation for inhalation, comprising the steps of:

micronizing a first active polar drug and a second active non-polar drug to form particles of them;

blending the particles of the second micronized non-polar active drug with particles of a polar excipient which are larger than the particles of both of the first and second micronized active drugs, to form an intermediate mixture; and blending the intermediate mixture with the particles of the first micronized active polar drug.

11. A method for preparing a dry powder formulation for inhalation, comprising the sequential steps of:

micronizing a first active drug having a first polarity and micronizing a second active drug having a second polarity which is less than the first polarity, to form particles of the first and second active drugs;

blending the second active drug particles with particles of an excipient having a polarity greater than the second polarity, to form an intermediate mixture, and with the particles of the excipient of a size greater than the first and second active drug particles; and blending the first active drug particles with the intermediate mixture.

12. A method for preparing a dry powder formulation for inhalation, comprising the steps of:

micronizing a first active drug having a first polarity to form particles of the first active drug;

micronizing a second active drug, to form particles of the second active drug, with the second active drug having a second polarity which is less than the first polarity;

blending the second active drug particles with particles of an excipient having a polarity greater than the second polarity, to form an intermediate mixture, and with the particles of the excipient of a size greater than the first and second active drug particles; and blending the first active drug particles with the intermediate mixture.

* * * * *